United States Patent [19]

Piazza et al.

[11] Patent Number: 6,046,216
[45] Date of Patent: Apr. 4, 2000

[54] METHOD OF TREATING A PATIENT HAVING PRECANCEROUS LESIONS WITH PHENYL PYRIDINONE DERIVATIVES

[75] Inventors: Gary Piazza, Highlands Ranch, Colo.; Rifat Pamukcu, Spring House, Pa.

[73] Assignee: Cell Pathways, Inc., Horsham, Pa.

[21] Appl. No.: 08/831,130

[22] Filed: Apr. 1, 1997

Related U.S. Application Data

[63] Continuation of application No. 08/488,187, Jun. 7, 1995, abandoned.

[51] Int. Cl.$^7$ ..................................................... A61K 31/44
[52] U.S. Cl. ..................... 514/340; 514/344; 514/345; 514/349; 514/351; 514/340
[58] Field of Search .................................. 514/344, 345, 514/349, 351

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/470 |
| 3,654,349 | 4/1972 | Shen et al. | 260/615 M |
| 3,780,040 | 12/1973 | Schnettler et al. | 260/256.5 |
| 3,812,127 | 5/1974 | Cronin et al. | 260/268 B |
| 3,819,631 | 6/1974 | Broughton et al. | 260/256.4 F |
| 3,920,636 | 11/1975 | Takahasi et al. | 260/240 J |
| 4,001,237 | 1/1977 | Partyka et al. | 260/256.4 B |
| 4,001,238 | 1/1977 | Partyka et al. | 260/256.4 B |
| 4,039,544 | 8/1977 | Broughton et al. | 260/256.4 F |
| 4,060,615 | 11/1977 | Matier et al. | 260/256.4 Q |
| 4,079,057 | 3/1978 | Juby et al. | 260/256.5 R |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/203 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 544/284 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,885,301 | 12/1989 | Coates | 514/263 |
| 4,923,874 | 5/1990 | McMahon et al. | 514/569 |
| 5,073,559 | 12/1991 | Coates | 514/263 |
| 5,147,875 | 9/1992 | Coates et al. | 514/263 |
| 5,223,501 | 6/1993 | Chakravarty et al. | 514/569 |
| 5,250,535 | 10/1993 | Verheyden et al. | 514/263 |
| 5,254,571 | 10/1993 | Coates et al. | 514/263 |
| 5,358,952 | 10/1994 | Moschel et al. | 514/569 |
| 5,401,774 | 3/1995 | Pamukcu et al. | 514/569 |

FOREIGN PATENT DOCUMENTS

| | | |
|---|---|---|
| 0 347146 A2 | 12/1989 | European Pat. Off. |
| 0 349239 A2 | 1/1990 | European Pat. Off. |
| 0 351058 | 1/1990 | European Pat. Off. |
| 0 352960 A2 | 1/1990 | European Pat. Off. |
| 0 395328 A2 | 10/1990 | European Pat. Off. |
| 0 428268 A2 | 5/1991 | European Pat. Off. |
| 0 463756 A1 | 1/1992 | European Pat. Off. |
| 0 485157 A2 | 5/1992 | European Pat. Off. |
| 0 485158 A2 | 5/1992 | European Pat. Off. |
| 0 485171 A2 | 5/1992 | European Pat. Off. |
| 0 485172 A2 | 5/1992 | European Pat. Off. |
| 0 485173 A2 | 5/1992 | European Pat. Off. |
| 0 508586 A1 | 10/1992 | European Pat. Off. |
| 0 526004 A1 | 2/1993 | European Pat. Off. |
| 0 607439 A1 | 7/1994 | European Pat. Off. |
| 56-53659 | 5/1981 | Japan . |
| 57-167974 | 10/1982 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |

OTHER PUBLICATIONS

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Onocology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, E. E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.—Band XXIX, S. 195–199 (1990).

Bjarnason et al., Gastroenterology, vol. 94, No. 4, pp. 1070–1074 (1988).

(List continued on next page.)

*Primary Examiner*—Jerome D. Goldberg
*Attorney, Agent, or Firm*—Robert W. Stevenson

[57] ABSTRACT

Derivatives of phenyl pyridinone are useful for the treatment of patients having precancerous lesions. These compounds are also useful to inhibit the growth of neoplastic cells.

13 Claims, No Drawings

OTHER PUBLICATIONS

Badrieh, Y., et al., Chem. Ber., vol. 125, pp. 667–674 (1992).

Silvola, J. et al., Effects of nonsteroidal anti-inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1998).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun. 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–9, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–51 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–35 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–12 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3',5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–17 (1992).

Radomski, Marek W. et al., Human Colorectal adenocarcinoma cells: differential nitric oxide synthesis determines their ability of aggregate platelets (Abstract Only), Cancer Res. 51(22) pp. 6073–8 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstact Only), J. Cardiovasc. Pharmacol. 18(2) pp. 237–42 (1991).

Souness, John E. et al., Role of Selective cyclic GMP phosphodiesterase inhibition in the myorelaxant actions of M&B 22,943, MY–5445, vinpocetine and 1–methy1–3–isobutyl–8–(methylamino)xanthine (Abstract Only), Br. J. Pharmacol. 98(3) pp. 725–34 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–51 (1989).

Mamytbekova, A., et al., Antimetastatic effect of flurbiprofen and other platelet aggregation inhibitors (Abstract Only), Neoplasma 33(4), pp. 417–21 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–71 (1984).

METHOD OF TREATING A PATIENT HAVING PRECANCEROUS LESIONS WITH PHENYL PYRIDINONE DERIVATIVES

This Appln is a cont't of Ser. No. 08/488,187 filed Jun. 7, 1995, Abdn.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, this invention is a method of treating a patient with precancerous lesions or neoplasms by administering a pharmacologically effective amount of the phenyl pyridinone derivative represented by the following formula (I), or the pharmacologically acceptable salt thereof;

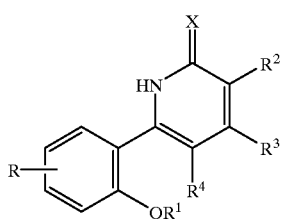

(I)

wherein X is O or S;

$R^1$ is $C_{1-6}$alkyl, $C_{2-6}$alkenyl, $C_{3-5}$cycloalkyl$C_{1-4}$alkyl, or $C_{1-4}$alkyl substituted by 1 to 6 fluoro groups;

$R^2$ is hydrogen, —CN, —CONR$^5$R$^6$, —CO$_2$R$^7$, 5-tetrazolyl, —NO$_2$, —NH$_2$ or —NHCOR$^8$ wherein R$^5$ to R$^8$ are independently hydrogen or $C_{1-4}$alkyl;

$R^3$ is hydrogen or $C_{1-4}$alkyl;

$R^4$ is hydrogen or $C_{1-4}$alkyl; and

R is halo, $C_{1-4}$alkyl, $C_{1-4}$alkoxy, cyano, —CONR$^9$R$^{10}$, —CO$_2$R$^{11}$, —S(O)$_n$C$_{1-4}$alkyl, —NO$_2$, —NH$_2$, —NHCOR$^{12}$, or —SO$_2$NR$^{13}$R$^{14}$ wherein n is 0, 1 or 2 and R$^9$ to R$^{14}$ are independently hydrogen or $C_{1-4}$alkyl;

with the proviso that $R^1$ is not methyl when $R^2$ is —CO$_2$H, —CO$_2$CH$_2$CH$_3$ or —CN, X is O, $R^3$ is hydrogen, $R^4$ is hydrogen or methyl and R is 6-methoxy.

Suitably X is S. Preferably X is O.

Suitably $R^1$ is $C_{2-6}$alkyl for example ethyl, n-propyl, isopropyl, butyl, isobutyl, pentyl or hexyl.

Suitably $R^1$ is $C_{3-5}$alkenyl for example allyl, butenyl or pentenyl.

Suitably $R^1$ is cyclopropylmethyl.

An example of $C_{1-4}$alkyl substituted by 1 to 6 fluoro groups is —CH$_2$CF$_3$.

Preferably $R^1$ is n-propyl.

Suitably $R^2$ is hydrogen, —CN, 5-tetrazolyl or —NO$_2$.

Suitably $R^2$ is —CONR$^5$R$^6$ wherein —NR$^5$R$^6$ is amino.

Suitably $R^2$ is —CO$_2$R$^7$ wherein $R^7$ is methyl.

Suitably $R^3$ is hydrogen or methyl.

Suitably $R^4$ is hydrogen or methyl.

Suitably R is halo for example fluoro, chloro, bromo or iodo.

Suitably R is $C_{1-4}$alkyl or $C_{1-4}$alkoxy for example methyl, ethyl, methoxy, ethoxy or propoxy.

Suitably R is cyano, —CONR$^9$R$^{10}$ for example —CONH$_2$, or —CONHCH$_3$ or —CON(CH$_3$)$_2$ or CO$_2$R$^{11}$ wherein R$^{11}$ is $C_{1-4}$alkyl.

Suitably R is —NO$_2$, —NH$_2$ or —NHCOR$^{12}$ wherein R$^{12}$ is $C_{1-4}$alkyl.

Suitably R is —S(O)$_n$C$_{1-4}$alkyl for example methylthio, ethylthio, methylsulphinyl, ethylsulphinyl, methylsulphonyl or ethylsulphonyl.

Suitably R is SO$_2$NR$^{13}$R$^{14}$ for example sulphamoyl, N-methylsulphamoyl or N,N-dimethylsulphamoyl.

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine. "Lower" refers to a number of carbon atoms of 6 or less.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer, and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

Preferable specific examples of the compound will now be described in order to facilitate the understanding of the present invention, though it is needless to say that the compounds of the present invention are not limited to these examples.

EXAMPLE 1

3-Cyano-6-(2-methoxy-4-methylthiophenyl)-2(1H)-pyridinone

A stirred mixture of 2-methoxy-4-methylthioacetophenone (7 g), dimethylformamide dimethyl acetal (5.9 ml) and dimethylformamide (21 ml) was heated under reflux for 16 hours then cyanoacetamide (4.5 g) was added and heating was continued for a further 12 hours. The mixture was diluted with water (100 ml), acidified with hydrochloric acid, and the resultant solid was digested with ethanol to give a crude product, 3.94 g. Purification by chromatography (silica, dichloromethane and dichloromethanemethanol mixtures) followed by recrystallization from acetonitrile yielded the pure title compound, 2.34 g, m.p. 245–247° C.

EXAMPLE (2a) AND (2b)

Ex. 2(a): 3-Cyano-6-(4-methylthio-2-propoxyphenyl)-2(1H)-pyridinone

Ex. 2(b): 1,2-Dihydro-6-(4-methylthio-2-propoxyphenyl)-2-oxo-3-pyridine carboxamide In a similar manner to that of Example 1, 4-methylthio-2-propoxyacetophenone (9.35 g) yielded a mixture which was separated to give 3-cyano-6-(4-methylthio-2-propoxyphenyl)-2(1H)-pyridinone, 3.24 g, m.p. 196–197° C. (from acetonitrile), and 1,2-dihydro-6-(4-methylthio-2-propoxyphenyl)-2-oxo-3-pyridine carboxamide, 0.25 g, m.p. 254–255° C. (from aqueous ethanol).

The starting material was prepared by the following method:

1-Bromopropane (18.19 ml) was added at room temperature to a stirred solution of the sodium salt from O-(4-acetyl-3-hydroxyphenyl)N,N-dimethylcarbamothioate (16 g) and sodium hydride (50%, 3.65 g) in dimethylformamide (180 ml). After 24 hours the mixture was diluted with water and extracted with ethyl acetate. The extract was washed with water and dilute sodium hydroxide. The residue left after evaporation was washed with water and petroleum ether to give O-(4-acetyl-3-methoxyphenyl)-N,N-dimethylcarbomothioate, which had m.p. 86–88° C. after trituration which hot aqueous ethanol. The above intermediate (18.35 g) was heated at 230–240° C. for 2 hours. A solution of the resultant solid in methanol (100 ml) and 5 normal sodium hydroxide solution (64 ml) was heated under reflux for 3 hours and then diluted with ethyl acetate. The mixture was extracted with dilute hydrochloric acid and evaporation of the organic layer gave 4-thio-2-propoxyacetophenone, 9.5 g, m.p. 80–82° C. Recrystallization from petroleum ether gave analytical material m.p. 83–85° C.

Methyl iodide (7.73 ml) was added to a solution of the above intermediate (9.0 g) and potassium hydroxide (7.18 g) in methanol (86 ml). After 30 minutes the mixture was diluted with ethyl acetate and washed with water. Evaporation gave 4-methylthio-2-propoxyacetophenone, 9.32 g, m.p. 55–57° C. after recrystallization from petroleum ether.

EXAMPLE 3

3-Cyano-6-(2-methoxy-4-methylsulphinylphenyl)-2(1H)-pyridinone

A solution of 3-cyano-6-(2-methoxy-4-methylthiophenyl)-2(1H)-pyridinone (1.24 g) in dichloromethane (500 ml) was treated with m-chloroperbenzoic acid (85%, 0.92 g). After 2 hours the solution was washed with sodium bicarbonate solution and evaporated to give the crude product (1.27 g, m.p. 239–241° C.). Purification by chromatography (silica, dichloromethane) followed by recrystallization from aqueous ethanol yielded the pure title compound, 0.81 g, m.p. 243–245° C.

EXAMPLE 4

3-Cyano-6-(4-methylsulphinyl-2-propoxyhenyl)-2(1H)-pyridinone

In a manner similar to that of Example 3, 3-cyano-6-(4-methylthio-2-propoxyphenyl)-2(1H)-pyridinone (0.98 g) yielded the title compound, 0.83 g, m.p. 183–184° C. (from acetonitrile).

EXAMPLE 5

3-Cyano-6-(4-methylsulphonyl-2-propoxyphenyl)-2(1H)-pyridinone

The product of Example 3 (0.66 g) in dichloromethane (50 ml) was treated with m-chloroperbenzoic acid (0.42 g) at room temperature. After 3 hours the solution was washed with sodium bicarbonate and the residue left after evaporation was triturated with water to give a solid, 0.61 g. Recrystallization from acetonitrile yielded the pure title compound, 0.2 g, m.p. 241–242° C.

EXAMPLE 6

3-Cyano-6-(2-methoxy-4-methylsulphonylphenyl)-2(1H)-pyridinone

In a manner similar to that of Example 3 but using an excess of m-chloroperbenzoic acid, 3-cyano-6-(2-methoxy-4-methylthiophenyl)-2(1H)-pyridinone (0.65 g) gave the title compound, 6.34 g, m.p. 280–282° C. (from acetonitrile).

EXAMPLE 7

3-Cyano-6-(5-fluoro-2-propoxyphenyl)-2(1H)-pyridinone

A stirred mixture of 3-dimethylamino-1-(5-fluoro-2-propoxyphenyl)-2-propene-1-one (2.46 g), cyanoacetamide (0.93 g), sodium methoxide (from 50% sodium hydride, 1.69 g, and methanol, 0.85 ml) in dimethylformamide (20 ml) was heated under reflux for 7 hours. The mixture was poured into water (150 ml) and acetic acid added to pH 4 to give a crude product. Recrystallization twice from acetonitrile gave a solid, 0.68 g, which was washed with petroleum ether and recrystallized again from acetonitrile to give the pure title compound, 0.15 g, m.p. 242–243° C.

The starting-material was prepared by the following method:

A stirred mixture of 5-fluoro-2-hydroxyacetophenone (10 g), potassium iodide (0.75 g) potassium carbonate (10.5 g), 1-bromopropane (6 ml) and acetone (100 ml) was heated under reflux for 30 hours. The filtered solution was evaporated and the residue was dissolved in dichloromethane and washed with dilute sodium hydroxide solution. Evaporation of the organic solution gave a crude product, Kugelruhr distillation (1 mm, 230–280° C.) of which gave 5-fluoro-2-propoxyacetophenone, 8.83 g, m.p. 58–60° C.

The above acetophenone (3.5 g) in dimethylformamide (20 ml) was heated under reflux with dimethylformamide dimethyl acetal (2.86 ml) for 48 hours. Additional dimethylformamide dimethyl acetal (1.5 ml) was added and the mixture was heated for a further 27 hours. After dilution with ethyl acetate (60 ml) the solution was washed with water, dried and evaporated. The residue was allowed to stand in the cold to give a solid which was triturated with petroleum ether to yield crude 3-dimethylamino-1-(5-fluoro-2-propoxyphenyl)-2-propene-1-one, 1.17 g, m.p. 43–46° C. Further material (1.9 g) was recovered from the filtrate.

EXAMPLE 8

1,2-Dihydro-6-(5-fluoro-2-propoxyphenyl)-2-oxo-3-pyridine carboxamide

The product of Example 7 (1.36 g) in a solution of potassium hydroxide (0.67 g) in water (15 ml) at 55° C. was treated with 30% hydrogen peroxide (6.5 ml) in portions during 4 hours. Additional potassium hydroxide solution was also added as required to maintain an alkaline solution. Acetic acid was added to pH 3 and the crude product was purified by flash chromatography (silica, chloroform) to yield 1.16 g of a solid m.p. 223–224° C. Recrystallization from aqueous ethanol gave the title compound, 1.04 g, m.p. 224–225° C.

EXAMPLE (9a) AND (9b)

Ex. 9(a): 3-Cyano-6-(4-methoxy-2-propoxyphenyl)-2(1H)-pyridinone

Ex. 9(b): 1,2-Dihydro-6-(4-methoxy-2-propoxyphenyl)-2-oxo-3-pyridine carboxamide In a similar manner to that of Example 1, 4-methoxy-2-propoxyacetophenone (7 g) yielded a mixture which was separated by flash chromatography to give 3-cyano-6-(4-methoxy-2-propoxyphenyl)-2(1H)-pyridinone, 2.6 g, m.p. 183–183.5° C. (from acetonitrile) and 1,2-dihydro-6-(4-methoxy-2-propoxyphenyl)-2-oxo-3-pyridine carboxamide, 0.22 g, m.p. 264–266° C. (from acetonitrile).

The starting material was prepared as an oil from 2-hydroxy-4-methoxyacetophenone by a similar method to that described in Example 7.

EXAMPLE 10

3-Cyano-6-(5-methoxy-2-propoxyphenyl)-2(1H)-pyridinone

In a similar manner to that of Example 1, 5-methoxy-2-propoxyacetophenone (7.7 g) gave 3.06 g of a crude product, 1.4 g of which was purified by flash chromatography to give the title compound, 0.9 g, m.p. 214–215° C. (from acetonitrile).

The starting material was prepared as a solid (m.p. 41–43° C.) from 2-hydroxy-5-methoxyacetophenone by a similar method to that described in Example 7.

EXAMPLE 11

1,2-Dihydro-6-(5-methoxy-2-propoxyphenyl)-2-oxo-3-pyridine carboxamide

In a similar manner to that of Example 8, 1.42 g of the crude product of Example 10 gave the title compound, 1.31 g, m.p. 199–201° C. (from acetonitrile).

EXAMPLE 12

3-Cyano-6-(5-cyano-2-propoxyphenyl)-2(1H)-pyridinone

In a similar manner to that of Example 1, 5-cyano-2-propoxyacetophenone (8.53 g) gave a reaction mixture which was poured into water (250 ml) and dichloromethane (350 ml). Filtration gave 1.62 g of a solid m.p. 248–251° C. The residue left after evaporation of the organic solution was digested with ether (3×10 ml) and the digest allowed to stand in the cold gave a further 1.45 g of solid m.p. 243–246° C. A portion of the crude product (1 g) was recrystallized from aqueous acetonitrile and then from acetonitrile to give the title compound, 0.65 g, m.p. 254–255° C.

The starting material was prepared as a solid m.p. 122–123° C. (from aqueous acetonitrile) from 5-cyano-2-hydroxyacetophenone by a similar method to that described in Example 7.

EXAMPLE 13

3-(3-Carboxamido-1,2-dihydro-2-oxo-6-pyidinyl)-4-propoxybenzamide

A stirred suspension of the product of Example 12 (0.66 g) in benzene (75 ml) was heated under reflux with manganese dioxide on silica (11.32 g, Synthesis, 1988, 715–717) for 18 hours. The cool mixture was filtered and the solid was digested twice with a hot mixture of methanol (100 ml) and concentrated aqueous ammonia (15 ml). Evaporation of the digest left a residue which was triturated with water to give 0.66 g of a solid, m.p. 275–277° C. This was combined with a further 0.2 g made in a similar manner and recrystallized twice from dimethylformamide to give the title compound, 0.45 g, m.p. 279–281° C.

EXAMPLE 14

Methyl-3-(3-cyano-1,2-dihydro-(2-oxo-6-pyridinyl)-4-propoxybenzoate

In a similar manner to that of Example 1, methyl 3-acetyl-4-propoxybenzoate (4.3 g) gave 1.1 g of a solid m.p. 201–203° C. Recrystallization from acetonitrile gave the title compound, 0.86 g, m.p. 203–204° C.

The starting material was prepared as follows:

A mixture of 5-cyano-2-propoxyacetophenone (9.6 g, prepared as in Example 12), acetic acid (90 ml) and concentrated hydrochloric acid (90 ml) was heated under reflux for 18 hours. The mixture was evaporated and the residue triturated with water to give 3-acetyl-4-propoxybenzoic acid, 9.7 g, m.p. 165–169° C.

The above acid (9.6 g) was esterified with methanol/sulphuric acid and the crude product was purified by flash chromatography to give methyl 3-acetyl-4-propoxybenzoate, 8.17 g, m.p. 44–47° C.

EXAMPLE 15

3-(3-cyano-1,2-dihydro-2-oxo-6-pyridinyl)-4-propoxybenzamide

A mixture of the product of Example 14 (1 g) and saturated methanolic ammonia (50 ml) was heated in a pressure vessel at 100° C. for 16 hours. Evaporation gave a crude product which after flash chromatography and recrystallization (aqueous ethanol) gave 0.22 g of the title compound contaminated with some unreacted starting material. This solid was combined with a further 0.28 g, made in a similar manner, and flash chromatography (silica, gradient elution using 5% methanol in chloroform and 1–5% ammonia) gave the title compound, 0.31 g, m.p. 246–247° C. (from aqueous ethanol).

EXAMPLE 16

N-Methyl-3-(3-cyano-1,2-dihydro-2-oxo-6-pyridinyl)-4-propoxybenzamide

A mixture of methyl 3-(3-cyano-1,2-dihydro-2-oxo-6-pyridinyl)-4-propoxybenzoate (2.0 g) and 1 Normal sodium hydroxide (30 ml) was heated under reflux for 45 minutes and the resultant solution was acidified to give a quantitative yield of 3-(3-cyano-1,2-dihydro-2-oxo-6-pyridinyl)-4-propoxybenzoic acid, m.p. 277–279° C. This acid was heated with thionyl chloride (10 ml) for 90 minutes, the solution was evaporated, and the acid chloride was dissolved in dichloromethane (60 ml). Methylamine was passed slowly through the stirred solution for 45 minutes and both the resultant solid and solution were washed with dilute hydrochloric acid and water. The solid was combined with the residue left after evaporation of the solution to give 1.66 g of solid m.p. 234–236° C. Recrystallization from ethanol gave the title compound, m.p. 235–237° C.

The starting material was prepared as follows:

A stirred mixture of 5-cyano-2-propoxyacetophenone (20.3 g), glacial acetic acid (150 ml) and concentrated hydrochloric acid (70 ml) was heated under reflux for 16 hours. The chilled mixture was then filtered and the collected solid was washed with water, then dissolved in dilute aqueous sodium hydroxide solution. Acidification of the filtered solution gave 3-acetyl-4-propoxybenzoic acid, 15.57 g, m.p. 177–179° C.

A stirred mixture of the above intermediate (14.34 g), methanol (200 ml) and sulphuric acid (2.0 ml) was heated under reflux for 20 hours. The residue after evaporation was distributed between water (150 ml) and dichloromethane (150 ml) and the organic layer was washed with water then aqueous potassium bicarbonate. The residue left after evaporation of the dried solution was triturated with petroleum ether to give methyl 3-acetyl-4-propoxybenzoate, 13.6 g, m.p. 55–56° C.

In a similar manner to that of Example 1, the above intermediate (13.5 g) gave 4.77 g of a solid which was purified to give methyl 3-(3-cyano-1,2-dihydro-2-oxo-6-pyridinyl)-4-propoxybenzoate, 4.14 g, m.p. 201–203° C.

EXAMPLE 17

N-Methyl-3-(3-carboxamido-1,2-dihydro-2-oxo-6-pyridinyl)-4-propoxybenzamide

In a similar manner to that of Example 13, N-methyl-3-(3-cyano-1,2-dihydro-2-oxo-6-pyridinyl)4-propoxybenzamide (0.45 g) gave 0.38 g of a crude product. Purification by flash chromatography and recrystallization from acetonitrile/methanol gave the title compound, 0.2 g, m.p. 286–288° C.

EXAMPLE 18

N,N-Dimethyl-3-(3-cyano-1,2-dihydro-2-oxo-6-pyridinyl)-4-propoxybenzamide

In a similar method to that of Example 16, methyl 3-(3-cyano-1,2-dihydro-2-oxo-6-pyridinyl)-4- propoxybenzoate (2.14 g) was saponified, converted into the acid chloride and treated with dimethylamine to give 2.0 g of a solid. This was combined with a further 0.2 g obtained in a similar manner, and purified by flash chromatography to give 1.9 g of solid m.p. 201–202° C. Recrystallization of part of this gave the title compound, m.p. 214–215° C.

EXAMPLE 19

N,N-dimethyl-3-(3-carboxamido-1,2-dihydro-2-oxo-6-pyridinyl)-4-propoxybenzamide

In a similar manner to that of Example 8, the product of Example 18 (1.1 g) gave 0.79 g of a solid which was purified by flash chromatography and recrystallization from acetonitrile/ethanol to give the title compound, 0.4 g, m.p. 203–204° C.

EXAMPLE 20

4-(3-Cyano-1,2-dihydro-2-oxo-6-pyridinyl)-3-propoxybenzonitrile

In a similar manner to that of Example 1, 4-acetyl-3-propoxybenzonitrile (3.6 g) gave 2.17 g of the title compound containing about 10% of the corresponding amide. A portion of the crude product (0.55 g) was heated under reflux with phosphoryl chloride (10 ml) for 90 minutes and the resultant solution was evaporated. The residue was treated with ice/water (50 ml) and the mixture was then stirred at room temperature for 30 minutes, neutralized with potassium bicarbonate, and filtered to give 0.48 g of a solid. Recrystallization twice from dimethylformamide gave the title compound, 0.2 g, m.p. 304–306° C.

The starting material was prepared as follows:

In a manner similar to that given in Example 7, 2-hydroxy-4-iodoacetophenone (9.27 g) gave 4-iodo-2-propoxyacetophenone, 6.97 g, m.p. 97.5–98.5° C.

A stirred mixture of the above intermediate (6.79 g) and cuprous cyanide (6.0 g) in 1,3-dimethyl-2-imidazolidinone (50 ml) was heated at 120° C. for 4 hours, then cooled and poured into a stirred mixture of aqueous potassium cyanide (21.78 g in water, 150 ml) and dichloromethane (200 ml). After 2 hours the organic layer was washed with water, dried, and evaporated to give 3.97 g of a solid. Purification by flash chromatography gave 4-acetyl-3-propoxybenzonitrile, 3.71 g, m.p. 99.5–100° C.

EXAMPLE 21

4-(3-Carboxamido-1,2-dihydro-2-oxo-6-pyridinyl)-3-propoxybenzamide

In a similar manner to that of Example 13, crude 4-(3-cyano-1,2-dihydro-2-oxo-6-pyridinyl)-3-propoxybenzonitrile (0.33 g) gave 0.33 g of a solid which was recrystallized from dimethylformamide to give the title compound, 0.22 g, m.p. 296–298° C.

EXAMPLE 22

3-Cyano-6-(5-methylthio-2-propoxyphenyl)-2(1H) pyridinone

In a manner similar to that of Example 1, 5-methylthio-2-propoxyacetophenone (7.75 g) gave 3.23 g of a solid, which was recrystallized in turn from acetonitrile, ethanol, and dimethylformamide to give the title compound, 0.26 g, m.p. 204–205° C.

The starting material was prepared as follows:

A solution of 3-acetyl-4-hydroxyphenyldiazonium chloride, prepared from 5-amino-2-hydroxyacetophenone (11.9 g) and hydrochloric acid (13.5 ml) in water (80 ml) with sodium nitrite (5.59 g) in water (15 ml), was added dropwise during 45 minutes to a stirred solution of potassium xanthate (17.7 g) in water (40 ml) at 70–75° C., then the temperature was raised to 90° C. for 30 minutes. Sodium hydroxide (10.0 g) was added and the stirred mixture was heated under reflux in an inert atmosphere for 18 hours. The cool mixture was acidified with 50% sulphuric acid, extracted with chloroform, and the combined extracts were washed with water and sodium bicarbonate solution. The residue left after evaporation was triturated with ether and some disulphide (2.88 g) was removed by filtration. Evaporation of the filtrate gave 7.86 g of a solid which was combined with a further 1.76 g of crude product obtained by stannous chloride reduction of the disulphide. Kugelruhr distillation (120–130° C., 1.0–0.7 mm Hg) gave 2-hydroxy-5-thioacetophenone, 7.15 g, m.p. 50–52° C.

Iodomethane (2.6 ml) was added dropwise to a stirred partial solution of the sodium salt prepared from the above intermediate (7.1 g) and 50% sodium hydride in oil (2.03 g) in dimethylformamide (35 ml). The resultant mixture was poured into water, hydrochloric acid added to pH 4, and the mixture was extracted with chloroform (4×50 ml). Evaporation of the washed and dried extract gave 7.95 g of an oil, flash chromatography of which gave 2-hydroxy-5-methylthioacetophenone as a pale yellow oil, 6.05 g.

In a manner similar to that given in Example 7, the above intermediate (6.75 g) gave 5-methylthio-2-propoxyacetophenone, 7.9 g, as a pale orange coloured oil.

EXAMPLE 23(a) AND 23(b)

Ex. 23(a): 3-(3-cyano-1,2-dihydro-2-oxo-6-pyridinyl) 4-propoxy-N,N-dimethylbenzenesulphonamide Ex. 23(b): 3-(3-Carboxamido-1,2-dihydro-2-oxo-6-pyridinyl)-4-propoxy-N,N-dimethylbenzenesulphonamide In a similar manner to that of Example 1, 3-acetyl-4-propoxy-N,N-dimethylbenzenesulphonamide (10.6 g) yielded a mixture which was separated to give 3-(3-cyano-1,2-dihydro-2-oxo-6-pyridinyl)-4-propoxy-N,N-dimethylbenzenesulphonamide, 3.74 g, m.p. 225–226° C. (from acetonitrile), and 3-(3-carboxamido-1,2-dihydro-2-oxo-6-pyridinyl)-4-propoxy-N,N-dimethylbenzenesulphonamide, 1,2 g, m.p. 250–252° C. (from aqueous ethanol).

The starting material was prepared by the following method:

A vigorously stirred mixture of 3-acetyl-4-hydroxybenzene sulphonic acid ammonium salt (29.5 g) and phosphoryl chloride (150 ml) was heated under reflux for 2 hours. The residue left after evaporation was very carefully added to 33% dimethylamine in ethanol (200 ml) cooled to 0° C. After the vigorous reaction had subsided the mixture was stirred for 2 hours at room temperature, allowed to stand overnight, and then evaporated. A solution of the residue in dichloromethane was washed with dilute hydrochloric acid and then extracted with 1 Normal sodium hydroxide solution (3×75 ml). Acidification of the extract gave a sticky solid which was purified by flash chromatography to yield 3-acetyl-4-hydroxy-N,N-dimethylbenzenesulphonamide, 14.0 g, m.p. 115–116° C. (from cyclohexane/toluene).

In a similar manner to that given in Example 7, the above intermediate (10.0 g) gave 3-acetyl-4-propoxy-N,N-dimethylbenzenesulphonamide, 10.94 g, m.p. 91.5–92° C. (from cyclohexane/toluene).

EXAMPLE 24

6-(2-Cyclopropylmethoxy-5-flourophenyl)-1,2-dihydro-2-oxo-pyridine-3-carboxamide In a similar manner to that of Example 8, 3-cyano-6-(2-cyclopropylmethoxy-5-fluorophenyl)-2(1H)-pyridinone (1.72 g) yielded the title compound, 1.08 g, m.p. 169–170° C. (from acetonitrile).

The starting material was prepared by the following method:

In a similar manner to that given in Example 7, but using cyclopropylmethylbromide, 5-fluoro-2-hydroxyacetophenone (8.5 g) yielded 2-cyclopropylmethoxy-5-fluoroacetophenone, 7.9 g, as a pale orange oil.

In a manner similar to that of Example 1, the above intermediate (7.8 g) yielded 3-cyano-6-(2-cyclopropylmethyl-5-fluorophenyl)-2(1H)-pyridinone, 3.05 g, m.p. 238–240° C.

EXAMPLE 25

6-(5-Fluoro-2-(2-methylpropoxy)phenyl)-1,2-dihydro-2-oxo-pyridine-3-carboxamide

In a similar manner to that of Example 8, 3-cyano-6-(5-fluoro-2-(2-methylpropoxy)phenyl)-2(1H)-pyridinone (1.88 g) yielded the title compound, 1.05 g, m.p. 193–194° C. (from acetonitrile).

The starting material was prepared by the following method:

In a similar manner to that given in Example 7, but using 1-bromo-2-methylpropane, 5-fluoro-2-hydroxyacetophenone (8.15 g) yielded 5-fluoro-2-(2-methylpropoxy)acetophenone, 5.1 g, as a pale brown semi-solid.

In a manner similar to that of Example 1, the above intermediate (7.0 g) yielded 3-cyano-6-(5-fluoro-2-(2-methylpropoxy)phenyl)-2(1H)-pyridinone, 2.28 g, m.p. 50–52° C.

EXAMPLE 26

3-Cyano-6-(2-propoxyphenyl)-2(1H)-pyridinone

A solution of 2-propoxyacetophenone (8.9 g) and ethyl formate (3.7 g) in diethyl ether (45 ml) was added dropwise over one hour to a cooled (<5° C.) suspension of sodium methoxide prepared from sodium hydride (2.4 g, 50% dispersion in oil) and dry methanol (2.05 ml) in anhydrous diethyl ether (45 ml). The mixture was stirred with cooling for 30 minutes and then stirred at ambient temperature overnight. The resulting mixture was extracted with water (4×15 ml) and the combined aqueous extracts were treated with cyanoacetamide (4.2 g) and a solution of glacial acetic acid (0.75 ml), water (3 ml) and piperidine (1.2 ml). The resulting mixture was heated under reflux for 2.5 hours, cooled and acidified with glacial acetic acid to afford a gum. The gum was washed with water and triturated with hot ethanol (40 ml) to afford the title compound as a cream powder, 3.22 g, m.p. 244°–247° C. A sample of this material (1.2 g) was recrystallized twice from dimethylformamide to yield the title compound as a white crystalline solid, 0.94 g, m.p. 245°–7° C.

EXAMPLE 27

6-(2-Propoxyphenyl)-1,2-dihydro-2-oxopyridine-3-carboxamide

30% Hydrogen peroxide (2.5 ml) was added dropwise over 10 minutes to a stirred solution of 3-cyano-6-(2-propoxyphenyl)-2(1H)-pyridinone (1.25 g) and potassium hydroxide (0.55 g) in water (10 ml). The mixture was warmed slightly and diethyl ether was added in order to control considerable frothing that was observed. The reaction mixture was then heated at about 45° C. for 1.5 hours, cooled and allowed to stand overnight at room temperature. A further sample of 30% hydrogen peroxide (1.5 ml) was added and the procedure as described above was followed until the reaction was complete. The cooled reaction mixture was neutralized with glacial acetic acid to afford a white precipitate (1.2 g) which was collected. This material was eluted from a silica column with dichloromethane/methanol (25:1) and the combined fractions containing product were evaporated to afford a cream coloured powder (0.92 g) which was recrystallized from absolute ethanol (20 ml) to afford the pure title compound, 0.81 g, m.p. 176°–8° C.

EXAMPLE 28

6-(2-Propoxyphenyl)-1,2-dihydro-2-oxopyridine-3-carboxylic acid

A solution of 3-cyano-6-(2-propoxyhenyl)-2(1H)-pyridinone (0.82 g) and absolute ethanol (1 ml) in 5 Normal potassium hydroxide (10 ml) was heated at 140° C. in a steel pressure vessel for 4 hours. The cooled mixture was acidified with concentrated hydrochloric acid to afford a cream solid which was collected. Thin layer chromatography indicated that this solid contained the required product together with an intermediate carboxamido compound and a trace of starting material. Thus, the solid was redissolved in 5 Normal potassium hydroxide (10 ml) and heated in a steel pressure vessel for 3 hours at 140° C. The cooled mixture was acidified with concentrated hydrochloric acid and the precipitated solid was collected, 0.90 g. The precipitate was recrystallized from aqueous ethanol to afford the title compound, 0.55 g, m.p. 194°–196° C.

EXAMPLE 29

6-(2-Propoxyphenyl)-1,2-dihydro-2-oxopyridine-3-carboxylate

A stirred mixture of 6-(2-propoxyphenyl)-1,2-dihydro-2-oxopyridine-3-carboxylic acid (0.9 g), dry methanol (30 ml), and 3 drops of concentrated sulphuric acid was heated under reflux for about 24 hours. The cooled mixture was evaporated to yield a pale yellow solid which was dissolved in chloroform, extracted with dilute aqueous potassium carbonate (2×10 ml), washed with water and brine, dried (magnesium sulphate) and evaporated to yield a yellow solid, 0.8 g, m.p. 126°–7° C. This was recrystallized from aqueous methanol (20 ml) to yield the pure title compound, 0.65 g, m.p. 126.5°–127.5° C.

EXAMPLE 30

6-(2-Propoxyphenyl)-3-(1H-tetrazol-5-yl)-2(1H)-pyridinone

A stirred mixture of 3-cyano-6-(2-propoxyhenyl)-2(1H)-pyridinone (1.85 g), sodium azide (0.59 g), ammonium chloride (0.49 g) and lithium chloride (0.39 g) in dry dimethylformamide (75 ml) was heated at 120° C. for 72 hours. The reaction mixture was evaporated to dryness and the resultant residue treated with water (100 ml) and acidified with glacial acetic acid to afford a precipitate which was collected and dissolved in warm dilute aqueous potassium bicarbonate. The aqueous solution was allowed to stand overnight at room temperature, was filtered and the filtrate was acidified with concentrated hydrochloric acid to afford a yellow precipitate, 1.80 g, m.p. 226°–230° C. This was recrystallized from ethanol (with charcoal) to afford the pure title compound, 1.08 g, m.p. 229°–231° C.

EXAMPLE 31

6-(2-Propoxylphenyl)-2(1H)-pyridinone 6-(2-Propoxyphenyl)-1,2-dihydro-2-oxopyridine-3-carboxylic acid (2.25 g) was heated at 300° C. under nitrogen for about 5 minutes. The cooled residue was partitioned between chloroform (50 ml) and dilute aqueous potassium carbonate (30 ml) and a small amount of insoluble material was removed by filtration. The organic phase was washed with dilute aqueous potassium carbonate, water and brine, dried (magnesium sulphate) and evaporated under reduced pressure to afford a yellow powder, 0.42 g. This material together with another sample (50 mg) similarly prepared was recrystallized from cyclohexane/toluene (10:1, 20 ml) to yield a cream solid, 0.27 g which was recrystallized twice from cyclohexane to afford the pure title compound, 0.19 g, m.p. 134°–135.5° C.

EXAMPLE 32

3-Nitro-6-(2-Propoxyphenyl)-2(1H)-pyridinone

A solution of 2-propoxyacetophenone (4.45 g) and ethyl formate (2.4 ml) in diethyl ether (20 ml) was added dropwise over minutes to a cooled (<5° C.) suspension of sodium methoxide prepared from sodium hydride (1.2 g, 50% dispersion in oil) and dry methanol (1 ml) in anhydrous diethyl ether (30 ml). The mixture was stirred with cooling for 30 minutes and then stirred at ambient temperature overnight. The resulting mixture was extracted with water (4×15 ml) and the combined aqueous extracts were treated with nitroacetamide (2.2 g) and a solution of glacial acetic acid (0.5 ml), water (2 ml) and piperidine (0.5 ml). The resulting mixture was heated under reflux for about 3 hours, cooled and acidified with glacial acetic acid to afford a gum. The gum was washed with water and triturated with warm ethanol (50 ml) to afford the crude title compound as a yellow powder, 0.60 g, m.p. 198°–200° C. This was recrystallized from acetonitrile to afford the pure title compound as yellow needles, 0.5 g, m.p. 201°–3° C.

EXAMPLE 33

3-Cyano-6-(2 methoxyphenyl)-2(1H)-pyridinone a) A stirred mixture of 2-methoxyacetophenone (5.5 ml) and dimethylformamide dimethylacetal (6.7 ml) in dry dimethylformamide (40 ml) was heated under reflux for 18 hours. A further quantity of dimethylformamide dimethylacetal (1 ml) was added and reflux continued for 3 hours. The cooled reaction mixture was diluted with ethyl acetate, washed with water and brine, dried (magnesium sulphate) and evaporated under reduced pressure yielding 3-dimethylamino-1-(2-methoxyphenyl)-2-propen-1-one as an orange oil. Further product remained in the aqueous extract which was evaporated under reduced pressure to yield a residue which was dissolved in ethyl acetate. The filtered solution was washed with water and brine, dried (magnesium sulphate) and evaporated under reduced pressure to yield a further quantity of orange oil. Total yield was 5.74 g.

b) A stirred mixture of 3-dimethylamino-1-(2-methoxyphenyl)-2-propene-1-one (5.74 g), cyanoacetamide (2.48 g) and sodium methoxide (from sodium hydride (50%, 4.32 g) and methanol (3.5 ml) in dry dimethylformamide was heated under reflux for 10 hours. The reaction mixture was poured into water, acidified to pH 4 with glacial acetic acid and extracted with ethyl acetate. The ethyl acetate extract was evaporated under reduced pressure to low volume and water was added to cause precipitation of a crude product (3.67 g) which was collected and recrystallized twice from dimethylformamide to yield the title compound, 1.68 g, m.p. 236°–238° C.

EXAMPLE 34

3-Cyano-6-(2-ethoxyphenyl)-2(1H)-pyridinone

In a similar manner to that of Example 26, 2-ethoxyacetophenone (2 g) yielded the title compound, 0.32 g, m.p. 262°–4° C. (from dimethylformamide).

EXAMPLE 35

3-Amino 6-(2-propoxyphenyl)-2(1H) pyridinone

A solution of 3-nitro-6-(2-propoxyphenyl)-2(1H)-pyridinone (0.3 g) in a mixture of ethanol (20 ml) and water (10 ml) containing 2 Normal sodium hydroxide (0.75 ml) was shaken with 10% palladium on charcoal (0.05 g) under hydrogen at atmospheric pressure until the uptake of hydrogen had ceased. The filtered solution was treated with dilute hydrochloric acid to pH 6 and evaporated to half its volume. Water (5 ml) was added and the mixture was filtered to give a crude product, 0.29 g, m.p. 158°–161° C. Recrystallization from 50% aqueous ethanol afforded the pure title compound, 0.11 g, m.p. 164.5°–165.5° C.

EXAMPLE 36

3-Cyano-4-methyl-6-(2-propoxyphenyl)-2(1H)-pyridinone

In a similar manner to that of Example 26, 2-propoxyacetophenone (8.9 g) was allowed to react with ethyl acetate in the presence of sodium methoxide, and the intermediate was cyclised with cyanoacetamide to give the title compound, 0.2 g, m.p. 180°–180.5° C. (from acetonitrile).

EXAMPLE 37

3-Cyano-5-methyl-6-(2-propoxyphenyl)-2(1H)-pyridinone

In a similar manner to that of Example 28, 2-propoxypropiophenone (9.6 g) gave the title compound, 3.0 g, m.p. 213°–214.5° C. (from acetonitrile).

EXAMPLE 38

3-Cyano-6-(2-(1,1,2,3,3,3-hexafluoropropoxy)phenyl-2(1H)-pyridinone

A stirred suspension of sodium hydride (0.024 g, 50% in oil) and 3-cyano-6-(2-hydroxyphenyl)-2(1H)-pyridine (1.06 g) in dimethylformamide (10 ml) was warmed to give a clear yellow solution. Hexafluoropropylene was passed through the solution at 10° C. until approximately 0.95 g was absorbed. The mixture was stirred at room temperature for 3 hours, allowed to stand overnight, then poured into water to give a solid, 1.69 g. Recrystallization from acetonitrile afforded the pure title compound, 0.4 g, m.p. 220°–222° C.

The starting material for the above was prepared in a similar manner to that of Example 26. Thus, 2-hydroxyacetophenone (10.2 g) yielded 3-cyano-6-(2-hydroxyphenyl)-2(1H)-pyridinone, 4.4 g, m.p. 317°–320° C. (from aqueous ethanol).

EXAMPLE 39

3-Cyano-6-(2-propoxyphenyl)-2(1H)-pyridinethione

2-Propoxyacetophenone (2.14 g) and dimethylformamide dimethylacetal (2 ml) were heated together in dimethylformamide (10 ml) at 130° C. for 18 hours. Cyanothioacetamide (1.6 g) was added, heating was continued for 2 hours, and the cool mixture was poured into water (100 ml). The aqueous mixture was neutralized with acetic acid and extracted with ethyl acetate. Evaporation of the extract gave a residue which was purified by medium pressure chromatography (silica, dichloromethane:methanol mixtures) to give a solid, 0.35 g, m.p. 127°–128° C. Recrystallization from aqueous ethanol afforded the pure title compound, 0.22 g, m.p. 130°–131° C.

EXAMPLE 40

1,2-Dihydro-4-methyl-2-oxo-6-(2-propoxyphenyl)pyridine-3-carboxylic acid

A mixture of 3-cyano-4-methyl-6-(2-propoxyphenyl)-2(1H)-pyridinone (0.75 g) and 5 normal potassium hydroxide (15 ml) was heated in a steel pressure vessel at 140° C. for 4 hours, then the cool solution was acidified with hydrochloric acid. A suspension of the resultant solid in aqueous hydrochloric acid (pH 1) was warmed on a steam bath for 20 minutes, cooled, and filtered to afford the title compound, 0.71 g, m.p. 175°–177° C.

EXAMPLE 41

1,2-Dihydro-4-methyl-2-oxo-6-(2-proposyphenyl)-pyridine-3-carboxylate

A mixture of 1,2-dihydro-4-methyl-2-oxo-6-(2-propoxyphenyl)pyridine-3-carboxylic acid (0.75 g), methanol (50 ml) and concentrated sulfuric acid (0.5 ml) was heated under reflux for 6 hours. The residue left after evaporation was treated with water (30 ml) and potassium carbonate was added to pH 10. The resultant solid was washed with water and with ether to afford the title compound, 0.6 g, m.p. 167°–169° C.

EXAMPLE 42

1,2-Dihydro-4-methyl-2-oxo-6-(2-propoxyphenyl-)pyridine-3-carboxamide 1,2-dihydro-4-methyl-2-oxo-6-(2-propoxyphenyl)-pyridine-3-carboxylate (0.53 g) and saturated methanolic ammonia (25 ml) was heated in a sealed vessel at 70°–85° C. for 34 hours. The residue after evaporation was triturated with methanol (10 ml) to give a solid, 0.28 g, m.p. 239°–242° C. Recrystallization from ethanol afforded the title compound, 0.18 g, m.p. 244°–246° C.

EXAMPLE 43

3-Cyano-6-(2-cyclopropylmethoxyphenyl)-2(1H)-pyridinone

A stirred mixture of 2-(cyclopropylmethoxy)-acetophenone (15 g), dimethylformamide (45 ml) and dimethylformamide dimethylacetal (12.75 ml) was heated at 140° C. for 25 hours, then cyanoacetamide (8.29 g) was added and the mixture was heated for a further 18 hours. The cool mixture was added to water (200 ml) and diethyl ether (100 ml) and the solid was collected by filtration, washed with water then with ethanol. Digestion with acetonitrile give the title compound, 6.1 g, m.p. 250°–252° C. (from acetonitrile).

EXAMPLE 44

6-(2-Butoxyphenyl)-3-cyano-2(1H)-pyridinone

In a similar manner to that of Example 43, 2-butoxyacetophenone (15.36 g) gave the title compound, 5.56 g, m.p. 218°–219° C. (from acetonitrile).

EXAMPLE 45

6-(2-Allyloxyphenyl)-3-cyano-2(1H)-pyridinone

In a similar manner to that of Example 43, 2-allyloxyacetophenone (15.84 g) gave the title compound, 7.76 g, m.p. 229°–230° C. (from dimethylformamide).

EXAMPLE 46

3-Cyano-6-[2-(2-methylpropoxy)phenyl]-2(1H)-pyridinone

In a manner similar to that of Example 43, 2-(2-methylpropoxy)acetophenone (15 g) gave the title compound, 3.96 g, m.p. 235° C. (from acetonitrile).

EXAMPLE 47

6-(2-Ethoxyphenyl)-1,2-dihydro-2-oxopyridine-3-carboxamide

30% Hydrogen peroxide (12.45 ml) was added during 1 hour to a stirred solution of the product of Example 34 (2 g) and potassium hydroxide (2.24 g) in water (20 ml) at 65° C. After a further 1 hour the mixture was acidified with hydrochloric acid to give the title compound, 2.06 g, m.p. 218°–220° C. (from ethanol).

EXAMPLE 48

6-(2-Cyclopropylmethoxyphenyl)-1,2-dihydro-2-oxopyridine-3 carboxamide

In a similar manner to that of Example 47, the product of Example 45 (2 g) gave the title compound, 2 g, m.p. 160°–161.5° C. (From acetonitrile).

EXAMPLE 49

6-(2-Butoxyphenyl)-1,2-dihydro-2-oxopyridine-3-carboxamide

In a similar manner to that of Example 47, the product of Example 46 (2.01 g) gave the title compound, 2.09 g, m.p. 190°–191° C. (from acetonitrile).

EXAMPLE 50

6-(2-Allyloxyphenyl)-1,2-dihydro-2-oxopyridine-3-carboxamide

In a similar manner to that of Example 47, the product of Example 47 (1.89 g) gave the title compound, 1.74 g, m.p. 210°–212° C. (from dimethylformamide).

EXAMPLE 51

6-(2-Methylpropoxyphenyl)-1,2-dihydro-2-oxopyridine-3-carboxamide

A stirred mixture of the product of Example 46 (1.39 g), manganese dioxide on silica gel (9 g) and benzene (150 ml) was heated under reflux overnight. Further manganese dioxide on silica gel (0.9 g) was added and the mixture was heated for another 3 hours. The mixture was filtered and the solid was washed with hot methanol. Evaporation of the benzene and methanol solutions gave the title compound, 1.39 g, m.p. 180° C. (from methanol).

EXAMPLE 52

1,2-Dihydro-5-methyl-2-oxo-6-(2-propoxyphenyl)-pyridine-3-carboxamide

In a similar manner to that of Example 47, the product of Example 39 (1.50 g) gave the title compound, 0.75 g, m.p. 238.5°–239.5° C. (from acetonitrile).

EXAMPLE 53

Pharmaceutical compositions for oral administration are prepared by combining the following:

|  | % w/w | | |
| --- | --- | --- | --- |
| 3-(3-Cyano-1,2-dihydro-2-oxo-6-pyridinyl)-4-propoxybenzamide | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 54

A pharmaceutical composition for parenteral administration is prepared by dissolving the title compound of Example 9(b) (0.02 g) in polyethylene glycol 300 (25 ml) with heating. This solution is then diluted with water for injections Ph. Eur. (to 100 ml). The solution is then sterilized by filtration through a 0.22 micron membrane filter and sealed in sterile containers.

It will be understood that various changes and modifications can be made in the details of procedure, formulation and use without departing from the spirit of the invention, especially as defined in the following claims.

What is claimed is:

1. A method of treating a patient having precancerous lesions sensitive to such a compound in the need of treatment, comprising administering to said patient to the patient a pharmacologically effective amount of a compound of the formula:

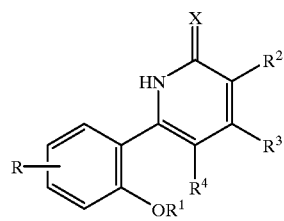

or a pharmaceutically acceptable salt thereof, wherein X is O or S;

$R^1$ is $C_{1-6}$alkyl, $C_{2-6}$alkenyl, $C_{3-5}$cycloalkyl$C_{1-4}$alkyl, or $C_{1-4}$alkyl substituted by 1 to 6 fluoro groups;

$R^2$ is hydrogen, —CN, —CONR$^5$R$^6$, —CO$_2$R$^7$, 5-tetrazolyl, —NO$_2$ or NHCOR$^8$ wherein $R^5$ to $R^8$ are independently hydrogen or $C_{1-4}$alkyl;

$R^3$ is hydrogen or $C_{1-4}$alkyl;

$R^4$ is hydrogen or $C_{1-4}$alkyl; and

R is hydrogen, halo, $C_{1-4}$alkyl, $C_{1-4}$alkoxy, cyano, —CONR$^9$R$^{10}$, —CO$_2$R$^{11}$, —S(O)$_n$C$_{1-4}$alkyl, —NO$_2$, —NH$_2$, —NHCOR$^{12}$, or —SO$_2$NR$^{13}$R$^{14}$ wherein n is 0, 1 or 2, and $R^9$ to $R^{14}$ are independently hydrogen or $C_{1-4}$alkyl.

2. The method according to claim 1 wherein X is O.

3. The method according to claim 1 wherein $R^1$ is $C_{2-6}$alkyl or $C_{3-5}$alkenyl.

4. The method according to claim 1 wherein $R^2$ is hydrogen, —CN, 5-tetrazolyl or —NO$_2$.

5. The method according to claim 1 wherein $R^2$ is —CONR$^5$R$^6$ wherein —NR$^5$R$^6$ is amino.

6. The method according to claim 1 wherein R is halo, $C_{1-4}$alkyl, $C_{1-4}$alkoxy, cyano, —CONR$^9$R$^{10}$ or —SO$_n$C$_{1-4}$alkyl.

7. A method of inhibiting the growth of neoplastic cells, comprising exposing said cells sensitive to such a compound to an effective amount of the compound of the formula:

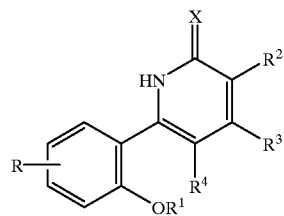

X is O or S;

$R^1$ is $C_{1-6}$alkyl, $C_{2-6}$alkenyl, $C_{3-5}$cycloalkyl$C_{1-4}$alkyl, or $C_{1-4}$alkyl substituted by 1 to 3 fluoro groups;

$R^2$ is hydrogen, —CN, —CONR$^5$R$^6$, —CO$_2$R$^7$, 5-tetrazolyl, —NO$_2$, —NH$_2$ or —NHCOR$^8$ wherein $R^5$ to $R^8$ are independently hydrogen or $C_{1-4}$alkyl;

$R^3$ is hydrogen or $C_{1-4}$alkyl;

$R^4$ is hydrogen or $C_{1-4}$alkyl; and

R is hydrogen, halo, $C_{1-4}$alkyl, $C_{1-4}$alkoxy, cyano, —CONR$^9$R$^{10}$, —CO$_2$R$^{11}$, —S(O)$_n$C$_{1-4}$alkyl, —NO$_2$, —NH$_2$, —NHCOR$^{12}$, or —SO$_2$NR$^{13}$R$^{14}$ wherein n is 0, 1 or 2 and $R^9$ to $R^{14}$ are independently hydrogen or $C_{1-4}$alkyl.

8. The method according to claim 7 wherein X is O.

9. The method according to claim 7 wherein $R^1$ is $C_{2-6}$alkyl, or $C_{3-5}$alkenyl.

10. The method according to claim 7 wherein $R^2$ is hydrogen, —CN, 5-tetrazolyl or —NO$_2$.

11. The method according to claim 7 wherein $R^2$ is —CONR$^5$R$^6$ wherein —NR$^5$R$^6$ is amino.

12. The method according to claim 7 wherein $R^3$ is hydrogen or methyl, and $R^4$ is hydrogen or methyl.

13. The method according to claim 7 wherein R is halo, $C_{1-4}$alkyl, $C_{1-4}$alkoxy, cyano, —CONR$^9$R$^{10}$ or —S(O)$_n$C$_{1-4}$alkyl.

* * * * *